(12) United States Patent
Srocka

(10) Patent No.: US 9,646,372 B2
(45) Date of Patent: May 9, 2017

(54) INSPECTION APPARATUS

(71) Applicant: HSEB Dresden GmbH, Dresden (DE)

(72) Inventor: Bernd Srocka, Berlin (DE)

(73) Assignee: HSEB Dresden GmbH, Dresden (DE)

( * ) Notice: Subject to any disclaimer, the term of this patent is extended or adjusted under 35 U.S.C. 154(b) by 0 days.

(21) Appl. No.: 14/650,273

(22) PCT Filed: Sep. 16, 2013

(86) PCT No.: PCT/EP2013/069156
§ 371 (c)(1),
(2) Date: Jun. 5, 2015

(87) PCT Pub. No.: WO2014/086511
PCT Pub. Date: Jun. 12, 2014

(65) Prior Publication Data
US 2015/0317783 A1    Nov. 5, 2015

(30) Foreign Application Priority Data

Dec. 5, 2012  (DE) ......................... 10 2012 111 835

(51) Int. Cl.
| | |
|---|---|
| G06K 9/00 | (2006.01) |
| G06T 7/00 | (2017.01) |
| G01N 21/88 | (2006.01) |
| H04N 5/247 | (2006.01) |
| G01N 21/95 | (2006.01) |
| G06T 7/30 | (2017.01) |
| G06T 7/70 | (2017.01) |

(52) U.S. Cl.
CPC ....... *G06T 7/0004* (2013.01); *G01N 21/8806* (2013.01); *G01N 21/9501* (2013.01); *G06T 7/30* (2017.01); *G06T 7/70* (2017.01); *H04N 5/247* (2013.01); *G01N 2201/02* (2013.01); *G01N 2201/12* (2013.01); *G06T 2207/10016* (2013.01); *G06T 2207/10048* (2013.01); *G06T 2207/20024* (2013.01); *G06T 2207/30148* (2013.01)

(58) Field of Classification Search
CPC . G06T 7/0004; G06T 7/0024; G01N 21/9501; G01N 21/8806
USPC ....................................................... 382/149
See application file for complete search history.

(56) References Cited

U.S. PATENT DOCUMENTS

| | | | |
|---|---|---|---|
| 6,791,680 B1 * | 9/2004 | Rosengaus ......... | G01N 21/9501 356/237.2 |
| 2004/0012775 A1 * | 1/2004 | Kinney .............. | G01N 21/9501 356/237.2 |
| 2011/0069154 A1 * | 3/2011 | Case .................. | G01N 21/9501 348/46 |

* cited by examiner

*Primary Examiner* — Ruiping Li
(74) *Attorney, Agent, or Firm* — Thorpe North & Western LLP

(57) ABSTRACT

An apparatus for inspecting flat objects, in particular wafers, containing an object holder; a camera arrangement having a camera for recording an image of at least one part of the object; and a drive arrangement for producing a relative movement between the camera arrangement and the object from a first recording position to at least one further recording position; is characterized in that the camera arrangement has at least one further camera; the object areas imaged in different cameras are at least partially different, wherein all cameras together simultaneously record only part of the total inspection area of the object; and each object point of the entire inspection area can be imaged at least once in one of the cameras as a result of the relative movement between the camera arrangement and the object, as produced with the drive arrangement.

18 Claims, 9 Drawing Sheets

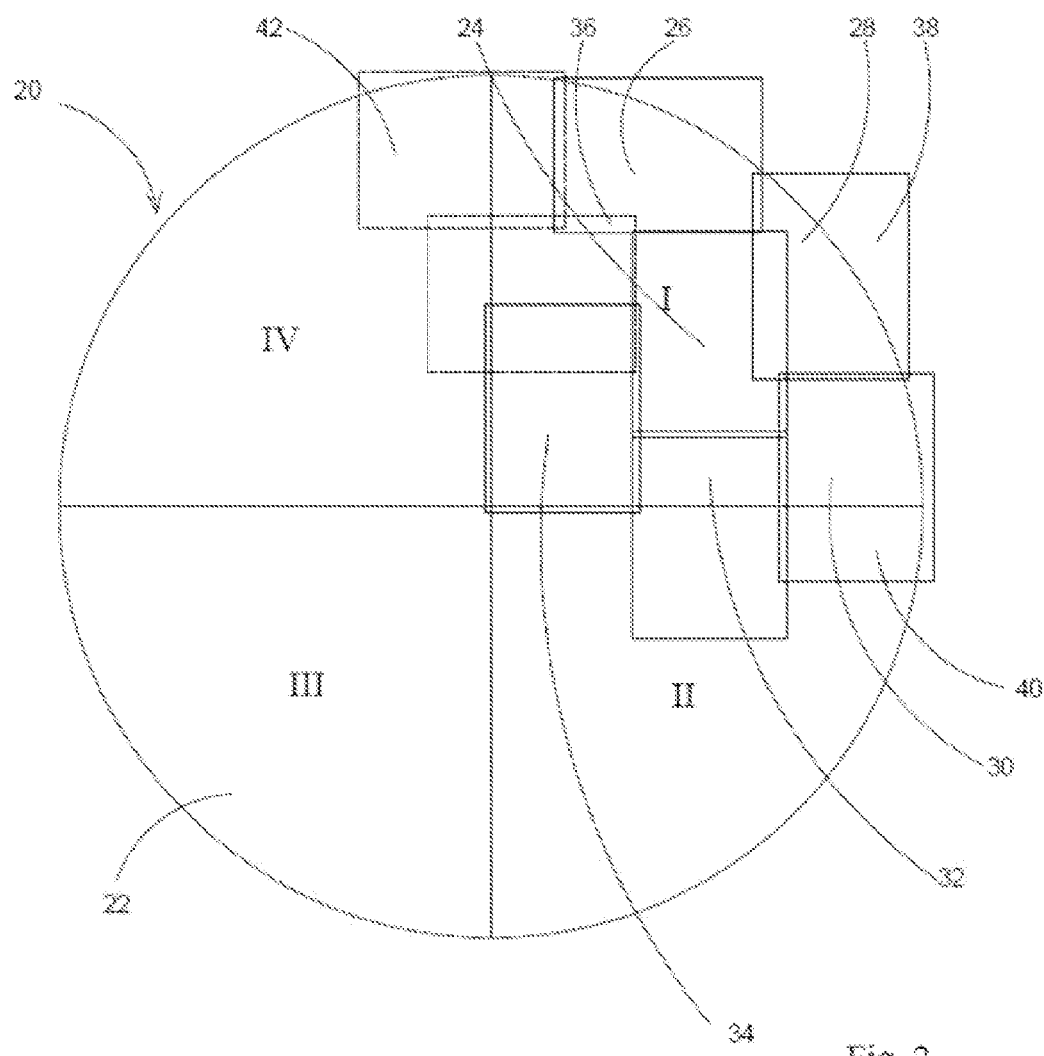
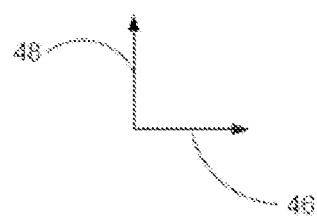
Fig. 2

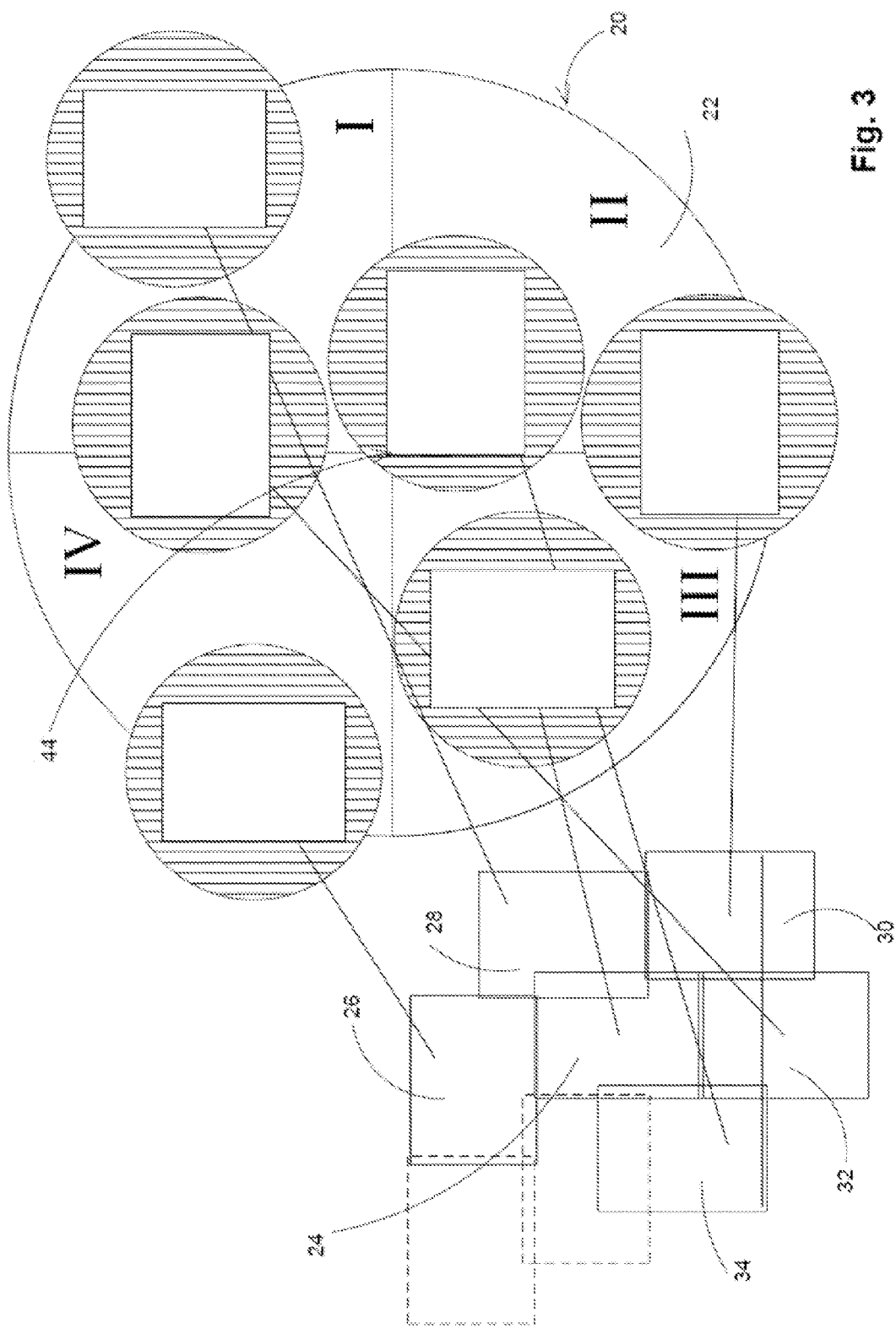

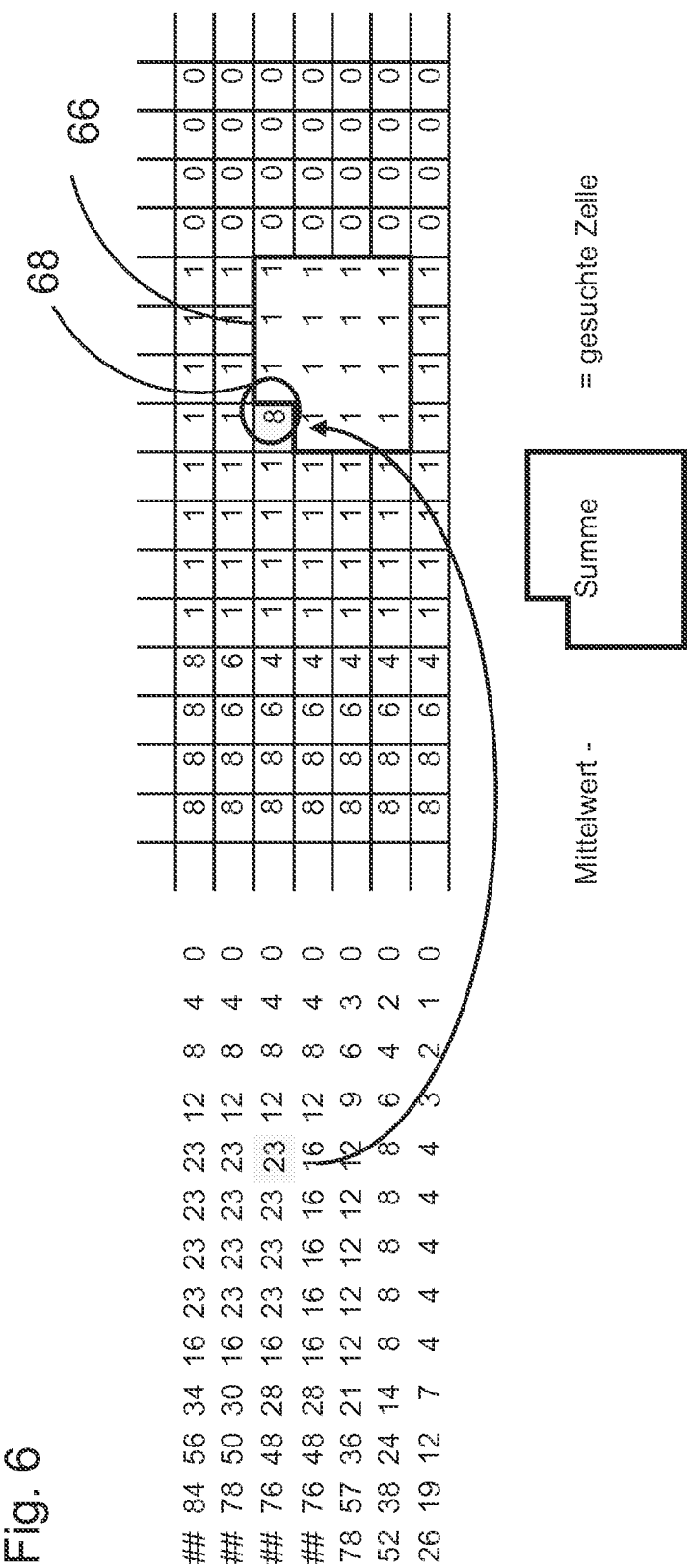

INSPECTION APPARATUS

TECHNICAL FIELD

The invention relates to a device for inspection of flat objects, in particular wafers, comprising:
an object holder
a camera assembly with a camera for taking an image of at least a portion of the object:
a driving assembly for the generation of a rotational movement between the camera assembly and the object from a first imaging position to at least one further imaging position:
wherein the camera assembly comprises at least one further camera;
wherein the object ranges imaged by different cameras are at least partly different, wherein all cameras together simultaneously detect only a portion of the same inspection range of the object;
each object point of the entire inspection range is imaged at least once by one of the cameras due to the rotational movement between the camera assembly and the object generated with the driving assembly; and
the object, the object holder or the camera assembly is rotatable about an axis perpendicular to the object plane of the cameras.

Furthermore, the invention relates to a method for inspection of flat objects, in particular wafers, comprising the steps of:
simultaneously taking images of at least partly different object ranges with different cameras of a camera assembly, wherein all cameras together simultaneously detect only a portion of the entire inspection range of the object;
generating a relative movement between the camera assembly and the object from a first imaging position to at least one further suitable imaging position, where a further portion of the inspection range is detected: and
repeating the above steps of taking images and generating a relative movement until each object point of the entire inspection range is imaged at least once by one of the cameras.

In different branches of the industry flat products are inspected for defects with optical imaging methods. In semiconductor- and solar cell industry these products are, amongst others, wafers. Wafers are discs of semiconductor-, glass-, sheet- or ceramic materials. The wafers are inspected in certain applications entirely or at least with large portions thereof. Such an inspection is called macro-inspection. The lateral resolution required for the detection of the interesting defects increases with developments of the general production technique. Typically, resolutions of 5 microns or less—up to as little as 1 micron—in macro-inspection are required for new technologies. At the same time devices having a high throughput of wafers for inspection are desirable. It is also desirable to have a possibility to increase the inspection throughput with decreased resolution requirements only by software changes.

Similar objects must be solved in different branches of the industry. In flat panel industry the displays must be inspected for defects in the production. Partly, imaging methods are used for the detection of defects imaging the entire display. When inspecting printed circuit boards in the electronic industry detects are detected with optical methods on series of specimen.

All such applications have in common that there is a need for quick inspection of a high number of objects which are normally of the same kind. Such objects are printed circuit boards, wafers, solar cells, displays and the like. They also have in common that sensors are used for the generation of large images of the objects. The images can be generated with optical imaging systems as well as with point-wise operating sensors depending on the kind of the detectable defects. Optical imaging systems are, for example, line and array cameras. Point-wise operating sensors are, for example, detectors for the measurement of the reflection of optical rays, microwaves or acoustic waves. Magnetic sensors may be used also.

Normally, the inspected objects are imaged by taking a plurality of pictures where the wafer and the imaging system are shifted relative to each other for each individual picture in order to inspect the entire wafer surface. Line cameras are used as well as detector arrays as imaging sensor.

Relative shifting between object and imaging system is effected step-wise or by continuous moving. A wafer or the camera is moved for step-wise shifting and stopped for taking the image. Images are taken during movement of the wafer with sufficiently short imaging- or illuminating time without stopping for continuous shifting. Different resolutions are achieved by using different objects with different magnification factors. All such methods have in common that the inspection of the entire wafer requires a plurality of images and mechanical movements. The inspection requires, therefore, considerable time. The inspection time increases by square with increasing resolution.

PRIOR ART

WO 2009 121 628 A2 (Nanda Tech) discloses a method for inspection of an entire wafer with one single image without moving the wafer. This solution is quick but has deficiencies regarding resolution of single small defects.

US 2011 069 154 A1 discloses an inspection system for rectangular solar cells. With such an inspection system several cameras are tightly mounted in a row (array) above the solar cells. The solar cells continuously move in one direction perpendicular to the row of cameras. The distance of the cameras is selected such that the fields of view slightly overlap and an image of the entire solar cell can be taken. The simultaneously taken images are digitally merged. The picture elements have a width in the range of 17 microns. A telecentric and a non-telecentric illumination is disclosed.

US 2011 006 9878 A1 discloses a two-dimensional camera array mourned above a printed circuit hoard which is moved without stopping. The publication explicitly describes that the method works without any expensive and complex devices for controlling any movements.

U.S. Pat. No. 6,791,680 B1 discloses an inspection assembly with an assembly of simple inspection devices simultaneously inspecting a wafer surface. Each device takes an image of a portion of the water surface. Furthermore, it is provided that the wafer or the assembly are moved in order to take images of the entire wafer surface. The publication discloses a movement in an X-direction as well as a movement in a Y-direction in order to reach the entire wafer with the inspection devices. The wafer is provided on a holder enabling a certain rotation. Such rotation is carried out to align the structures on the wafer parallely to the scanning direction of the inspection devices.

US 2011 016 5095 A1 discloses an infrared transmission inspection assembly for wafers. Two line cameras are moved in one direction above the wafer while the water moves in a perpendicular direction. The entire width of the sample is covered with two line detectors.

U.S. Pat. No. 5,848,123 discloses a method in the medical area for detecting an object with a moving sensor. The publication describes how an increased sensitivity can be obtained by binning while compromising the resolution.

WO 97/1337 discloses an inspection method with a camera in the form of a linear diode array.

US 2003/0218741 A1 discloses an inspection device with two inspection heads having a different resolution. The images of the inspection head with the smaller resolution are used to find positions which must be inspected with higher resolution.

DISCLOSURE OF THE INVENTION

It is an object of the invention to provide a device of the above mentioned kind, which enables an inspection in shorter time with higher accuracy.

According to an aspect of the invention this object is achieved in that the inspection range is arranged one plane and formed by a surface of the object perpendicular to the rotational axis (44) of the rotational movement, and the image of the imaging fields of different cameras in the camera assembly taken in different imaging positions are assembled to a common overall image.

Furthermore, the object is achieved with a method for inspection of flat objects, in particular wafers, which is characterized in that the relative movement front a first imaging position to at least one further imaging position is a rotation of the camera assembly or of the object about an axis perpendicular to the object plane of the camera.

The invention uses several cameras in one camera assembly. The cameras have a fixed position within the camera assembly. Accordingly, the cameras are moved all together from one imaging position to another imaging position. The use of several cameras has the effect that very many image points are simultaneously detected and processed. Thereby the inspection duration is decreased compared to known assemblies. The assembly requires one driving system only for the entire camera assembly or the object, respectively. The time required for fine-adjustment is, therefore, also shorter than with known assemblies.

In a preferred modification of the invention the cameras of the camera assembly are statically mounted. The object is then moved from one imaging position to another imaging position. It is understood, however, that the object may have a statical position and that the camera assembly is moved from one imaging position to another imaging position.

In a particularly preferred modification of the invention the object, the object holder or the entire camera assembly are rotatably mounted about an axis perpendicular to the object plane of the cameras. Since the images are processed during operation as fine adjustment is not required. For example, six cameras can be used. An object range is imaged by each of the six cameras. The object ranges and the camera positions are selected such that a rotation will provide that new object ranges are imaged by the cameras which have not been imaged before. If the area of about a quadrant of the object is imaged by the cameras in one imaging positions the entire object can be inspected with three further imaging positions. The condition is that the object ranges are imaged in different relative sections within a quadrant. It is not necessary, that all object ranges of one imaging position are in the same quadrant, as long as they complement each other with three further rotations and fully cover the quadrant.

The use of 6 cameras with a side relation of 4:3 with 4 imaging positions has been proven to be particularly advantageous for the inspection of currently common wafer sizes. It is understood, however, that different relations and sizes can be chosen. They can be optimized depending on the amount of cycles, the size of the wafer, the side relation of the sensor arms of the cameras and the desired resolution for achieving a short inspection duration.

In a further advantageous modification of the invention, the cameras are provided with a plurality of detector elements (pixels) and the object, the object holder, the sensor chips with the detector elements inside the cameras or the entire camera assembly are shiftable in the object plane by a distance, where a multiple of such distance corresponds to the length of the detector elements in the direction of the shifting distance. Such shifting in a sub-pixel range can be used to obtain an image with a resolution which is higher than the resolution provided by the diameters of the detector elements of the detector.

Preferably, the object, the object holder, the sensor-chips with the detector elements inside the cameras or the entire camera assembly are shiftable several times in two perpendicular directions in the object plane by distances where a multiple of such distances corresponds to the length of the detector elements in the direction of the corresponding shifting distances. Thereby, the resolution can be increased in two directions.

Preferably, each camera of the camera assembly is provided with its own imaging optical assembly and its own detector. The images may be essentially telecentric.

Further modifications of the invention are subject matter of the subclaims. An embodiment is described below in greater detail with reference to the accompanying drawings.

BRIEF DESCRIPTION OF THE DRAWINGS

FIG. 2 is a top view of a wafer and illustrates the arrangement of image fields in one quadrant of the wafer.

FIG. 3 shows an example for the arrangement of FIG. 2 in a first imaging position.

FIG. 4a-e illustrates how shifting the wafer is effected in a sub-pixel range.

FIG. 6 shows a detail of FIG. 5.

DESCRIPTION OF THE EMBODIMENT

Figure 1:
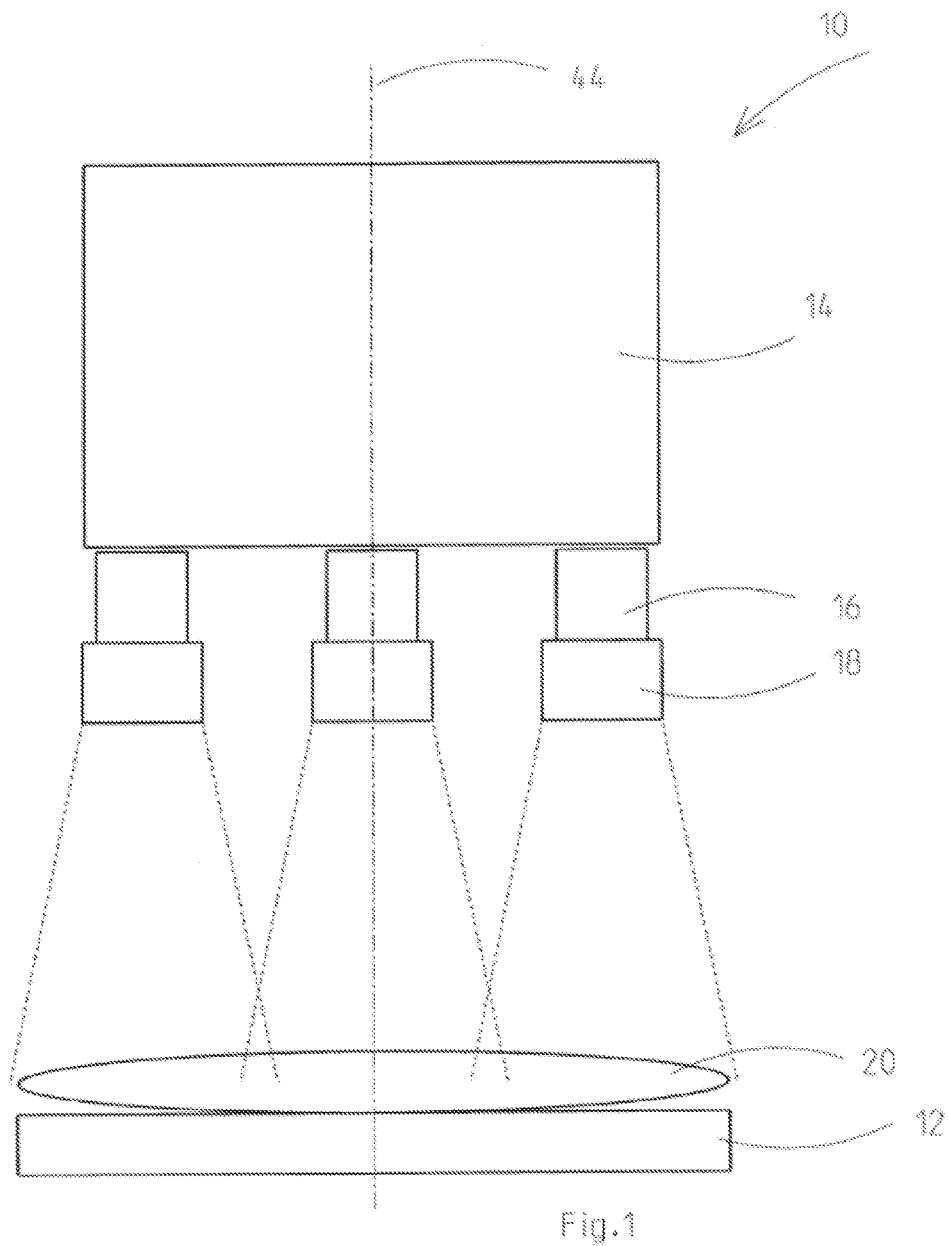
FIG. 1 is a schematic view of an inspection device with several cameras.

FIG. 1 is a schematic representation of an inspection device which is generally denoted with numeral 10. The inspection device 10 is provided with a table 12. Wafer 20 or different inspection objects are moved onto the table by means of a handling system (not shown). A camera assembly 14 is mounted above the table 12. The camera assembly 14 is fixed to a housing and statically mounted. The camera assembly is provided with 6 cameras 16. Each of the cameras 16 has its own detector and its own imaging optical assembly 18. In the present embodiment the magnification is 1:2. The detectors used in the cameras 16 are identical and have 5344×4008, i.e. 21.4 mio detector elements per camera. The side relation of the detectors is 4:3 corresponding to the middle image format 28 mm×37 mm. Each detector element has at side width of 7 microns.

FIG. 2 corresponds to a top view on a typical wafer 20. The wafer 20 can be divided in four quadrants 22 with identical form and area. The quadrants 22 are designated with I, II, III and IV. It can be shown theoretically that the area of such a quadrant can be fully detected with the 6 cameras 16 of the camera assembly 14. In other words: There is at least one arrangement of 6 image fields 24, 26, 28, 30, 32 and 34 covering a quadrant 22 of the wafer 20 without gaps without too many overlapping areas 36 and unused detector area 38 outside the wafer. Image fields 40 extending beyond one side of the quadrant will cover the missing area 42 at the other side in terms of area.

Such finding is used for the selection of the camera positions within the camera assembly 14. Each of the six cameras obtains a position corresponding to one of the image fields 24, 26, 28, 30, 32 and 34 described above. Not all image fields from the same quadrant are imaged by the cameras, but the cameras are distributed along the entire wafer above different quadrants. An example of such an arrangement is shown in FIG. 3 for a first imaging position. Thereby, it is achieved that there is sufficient space for object lenses, cameras, holders etc. The mounting space available for each camera-object lens combination is represented by a circle.

The image field 28 is imaged by a camera which is mounted in the first imaging position as shown in FIG. 3 above quadrant designated with I. The image field 24 is imaged by a camera which is mounted in the first imaging position above quadrant designated with III. The image field 26 is imaged by a camera which is mounted in the first imaging position above quadrant designated with IV. The image field 30 is imaged by a camera which is mounted in the first imaging position above quadrants designated with II and III. The image field 32 is imaged by a camera which is mounted in the first imaging position above quadrants designated with I and IV. The image field 34 is imaged by a camera which is mounted in the first imaging position above quadrant designated with III.

After imaging in the first imaging position the table 12 is rotated about its center axis 44 perpendicular to the wafer surface. In the present embodiment where the division of the wafer is effected with four quadrants the rotation is made about 90°. If the wafer is divided in sextants the rotation is made about 60°. After clock-wise rotating about 90° the camera with the imaging field 24 is arranged above the quadrant II. Accordingly, the other five cameras are arranged about the respective adjacent quadrant. Thereafter, images are taken again in the second imaging position. This procedure is repeated three times altogether until each camera 16 was positioned above each quadrant 22 once.

In such a way four imaging positions and six cameras 16 will generate 4×6=24 images altogether. They are joined together during processing with a software to become one overall image. With parallel processing of the data generated by the cameras the image is generated very quickly. The only movement for such procedure is the rotation of the table. Since several cameras 16 are available enabling the determination of the camera position relative to the wafer, no fine adjusting of the table position or the rotation angle after a rotation is necessary. Thereby, the inspection duration is further decreased.

As the entire imaging sequence only requires 3 movements it can be carried out very quickly in about, for example, 10 seconds. A high throughput can be, therefore, realized for such basic resolution.

With the described embodiment a pixel-resolution of about, for example, 14 microns can be achieved with commercially available cameras, such as, for example, a 22 MP camera. The method can be scaled to any object form and sized by suitable choice of amount and arrangement of the cameras and suitably chosen object lenses. In particular, it can be adapted to all wafer sizes which are used in semiconductor industries or planned for the future.

The present inspection device 10 enables the generation of a wafer image with particularly high resolution. In order to achieve this the wafer table 12 with the wafer 20 is moved in each of the imaging positions four times in a lateral direction to the right in the direction of arrow 46 in FIG. 2 and four times upwards in the representation in the direction of arrow 48 in FIG. 2 and an image is taken. A Piezo driver can be used for the movement. The movement is effected for a distance which corresponds to a quarter of the length of a detector element. In such a way four values are generated in each imaging position by each detector element. Each value represents the average value of the gray value at the respective imaging position. From the image stack with images shifted by sub-pixel steps obtained in such a way an image with the resolution of the sub-pixel step width can be calculated with mathematical methods.

Figures 4A, 4B, 4C:
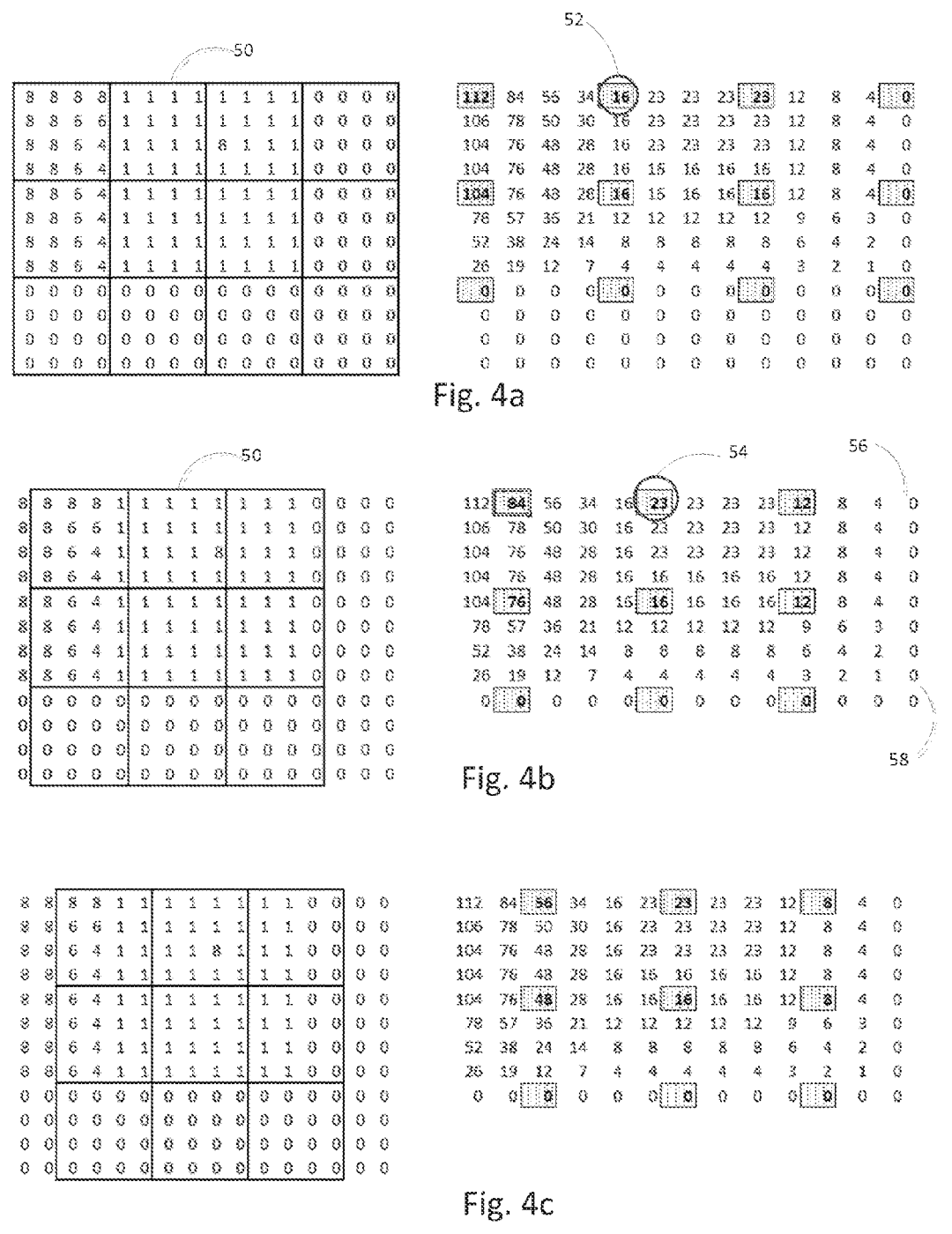

The imaging method is represented in FIG. 4a-e by means of a number example. Assuming that each objective lens 18 in an image images with as resolution of a quarter of the size of a detector element the detector will detect in a basic position the gray values as shown in FIG. 4a on the left. The detector element is represented by a square 50 therein. The gray values caused by the sub-pixel shift are designated by 4×4 numbers 52 within said square. The camera integrates about all of such 4×4 values whereby the first camera image consists of the values 52 highlighted on the right side in FIG. 4a which are on the upper left in the fields 50.

Figures 4D, 4E:
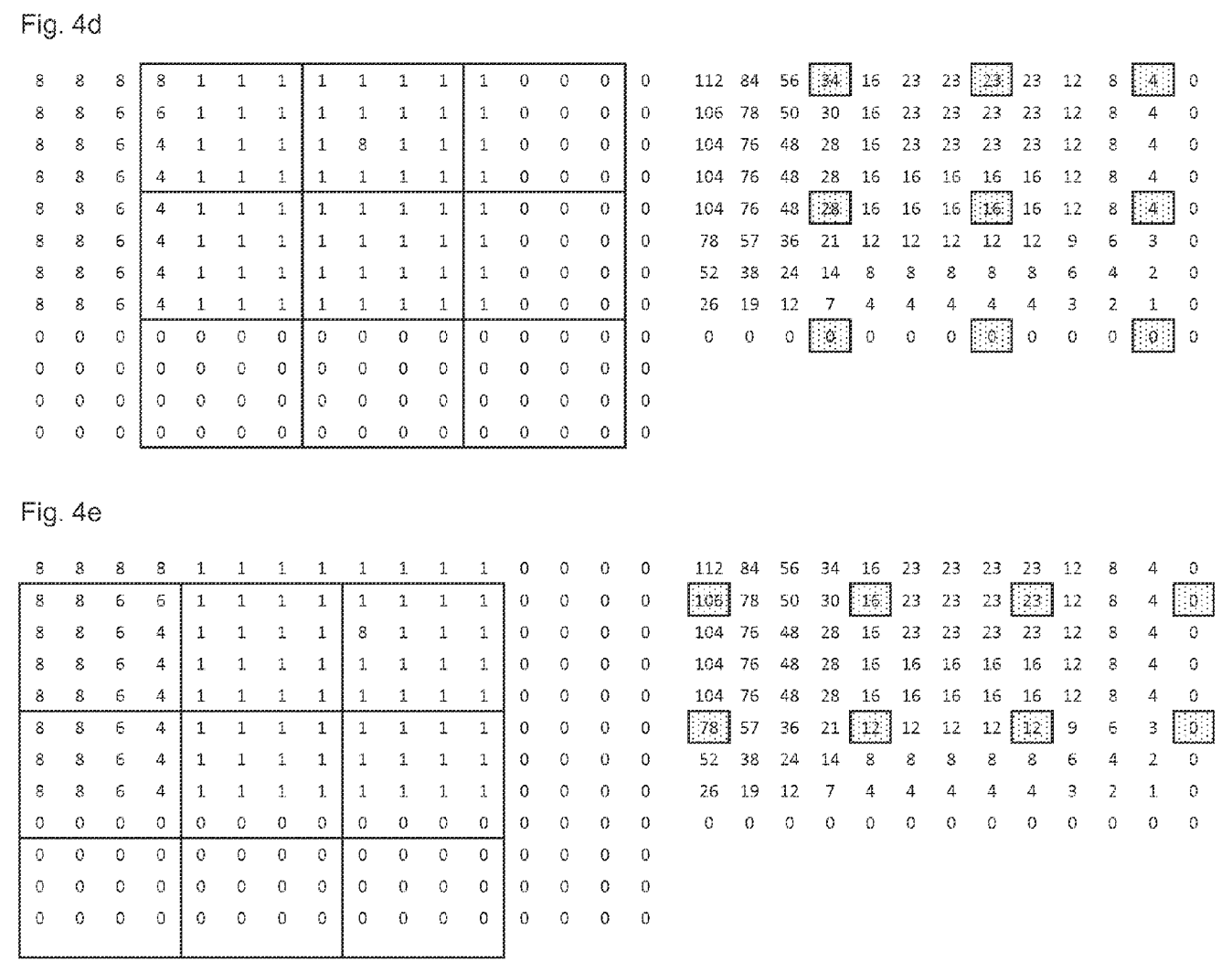

The wafer 20 is then shifted relative to the camera 16 that the image moves towards the left by ¼ of a detector element. The camera 16 then takes an image as shown in FIG. 4b. The values 54 with gray background form the 2 camera image. FIGS. 4c and 4d show the representations of the 3, and 4, image. In FIG. 4e the 5th image is shown which is taken according to the same principle with a vertical shifting direction. Overall, 4×4=16 images are taken in this example at positions which are shifted by ¼ of the length of a detector element.

The image stack taken in such a way is joint to an image in the right side of FIGS. 4a to 4e. The image stack represents a 2-dimensional, moving average of the original gray values with a smoothing width of 4 values. The original value grating on the left side of FIGS. 4a to 4e can be fully derived from such an average. For this purpose, at least two edges 56 and 58, i.e. one vertical and one horizontal, the last line and the last column are taken with well defined known tray values. In the present case, such gray values are 0.

Figure 5A:
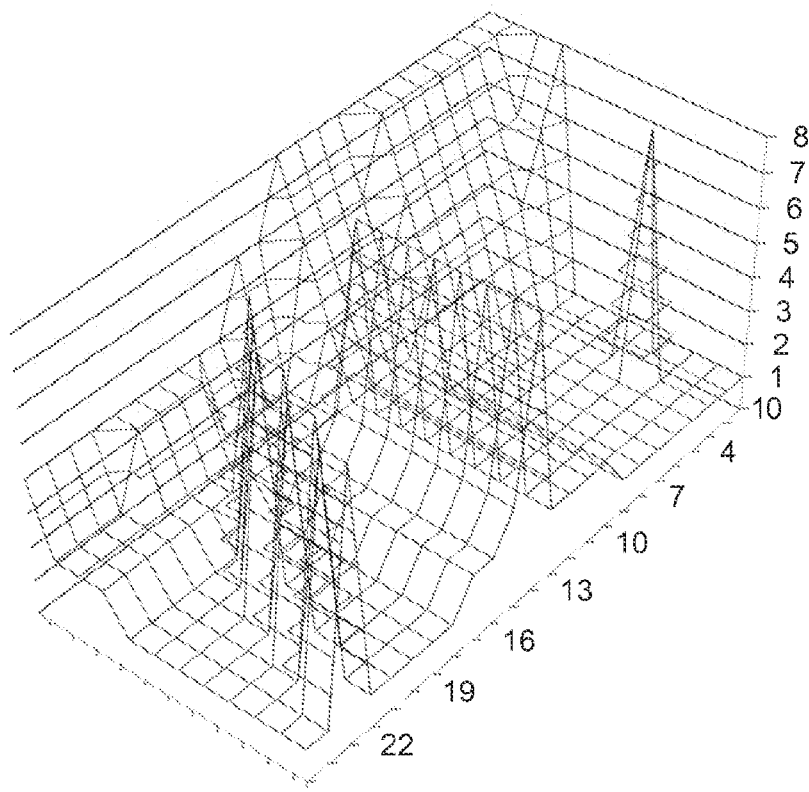
FIG. 5a-c illustrates with a computer simulation how the image of a wafer is reconstructed.
Figure 5B:
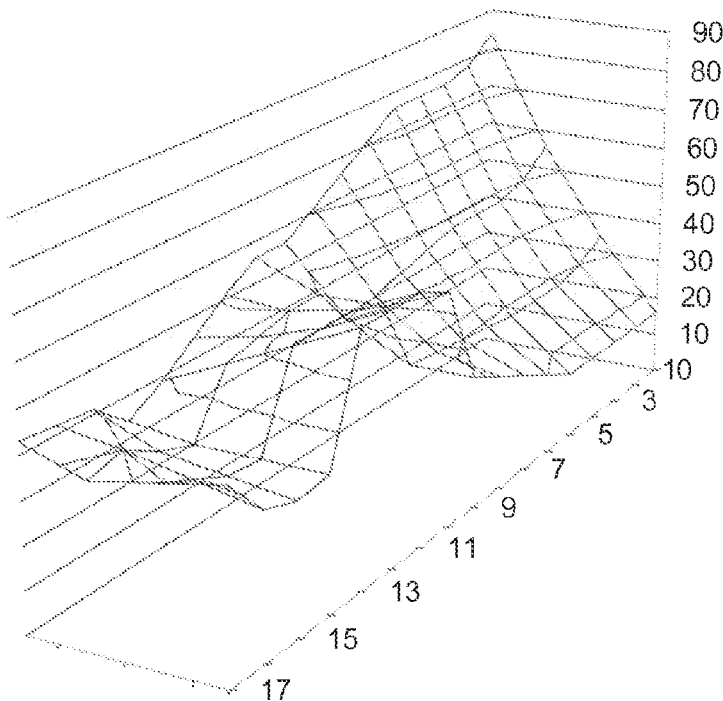
Figure 5C:
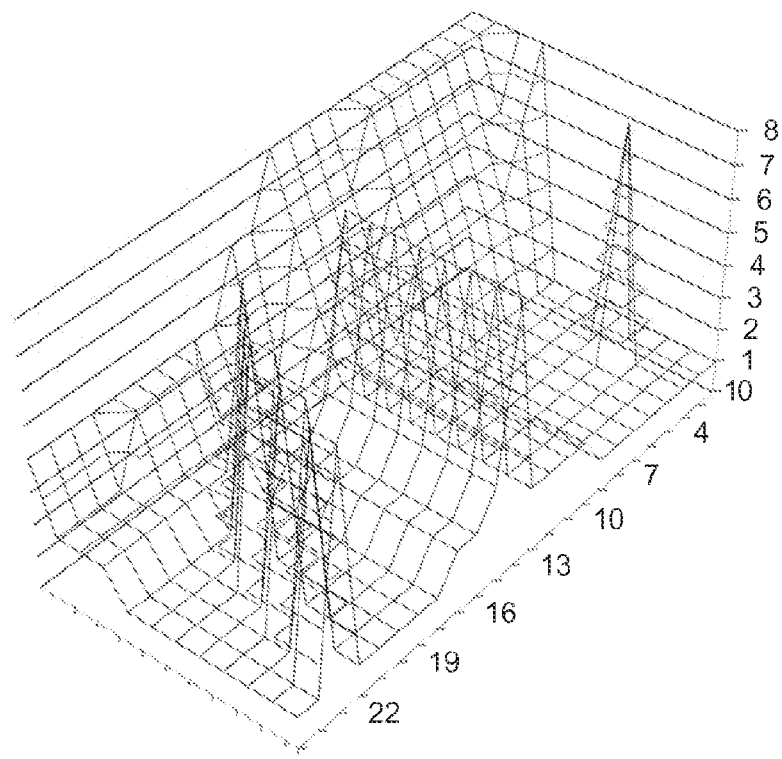

The reconstruction starts at such known edges 56 and 58 and mathematically represents a simple 2-dimensional differential calculation. The offset which remains unknown after the differential calculation is calculated from the known edges. This is shown with the example of a simulation in FIG. 5 FIG. 5a shows the original image 60. FIG. 5b is the average image 62 assembled from the individual images taken with the camera. FIG. 5c shows the reconstructed image 64. The value of each individual detector element in a high resolution reconstructed image 64 results from the corresponding value in the average image 62 minus the values already calculated in the 15 cells 66 in the 4 rows on the right and below the considered detector element 68 as shown in FIG. 6.

Using the described imaging method it is possible to increase the effective resolution of the image by suitably choosing the amount of sub-pixel steps down to the resolution limit of the objective lens. The cameras don't need a much higher number of detector elements and must not be scanned over the wafer with much efforts.

A simple and very flexible selection is possible between a very high throughput and a very high resolution. In order to achieve a high throughput only the 4×6 "basic images" are taken without sub-pixel shifting. In order to achieve a very high resolution sub-pixel shifted images are taken in addition to each quarter rotation of the wafer.

In the present embodiment the cameras have a high grey value resolution and small noise. By careful processing of the grey values it is possible to detect defects below the objective lens resolution even if they cannot be resolved in an optical sense. With cameras having 12 bit resolution more than 4000 grey values are available. With a noise level of the camera below 10 grey values a defect assumed as being square can be detected with a contrast of, for example, 30 grey values relative to the environment.

In the above described, simple embodiment black and white cameras were used. For more complex inspections with simultaneous high throughput requirements 3-CCD cameras or black and white cameras with additional full-area color filters are used for particularly high flexibility. In the latter case a filter changer can carry 2, 3 or even more filters for each camera, for example. They can be simultaneously moved in front of the camera sensors in one step. By using separate filters which are introduced independently of the camera the wavelength ranges can be adapted to the respective application. Thereby, it is possible to use near infrared filters in order to transmit, for example, thin silicon layers in addition to common red, green and blue-filters.

The images taken according to the above described steps can be processed by all common and known methods for defect recognition from image data. In particular the is known methods of comparing with a reference or local comparison or the comparison with a reference generated from a production data basis can be used.

A color image can be generated at first for different application cases which is then compared to a reference image. Also it is advantageous to carry out a local image comparison with repeating structures in the same image due to the large image fields. This method is particularly robust against brightness—and color variations of the used light source as well as against positioning inaccuracies of the inspected wafer.

Alternatively the detected partial images can be inspected at first in the individual color channels regarding defect signatures in order to process, for example, only such defects in greater detail which are visible in at least 2 or at least 3 color channels.

In an alternative embodiment a camera assembly is used only with one camera. The camera is not rotated but only shifted about the above described path which is smaller than one pixel length. A piezo element is suitable for such a purpose. The shifting path can be very accurately adjusted. The element is only required for the sub-pixel shifting and is not used for moving the object otherwise. Contrary to known devices a very high adjustment accuracy and high resolution is achieved with little costs. The high resolution image is determined as described above.

In a further, alternative embodiment, several stationary cameras are used which are shifted against each other by a path in the sub-pixel range.

It can be recognized that the images shifted by a path in sub-pixel range are either obtained by imaging and shifting the object or the camera in a time sequence and/or by simultaneous imaging with several cameras which are shifted against each other by a path in sub-pixel range. In any case several images are taken of the same object range which can be assembled to one image with an increased resolution by calculation.

All such modifications do not constitute a deviation of the invention and depend on the special requirements of the respective application.

The above description was given for better understanding using an example with precise data regarding the amount of image points, the size of the section and the formation of average values and threshold values. It is understood, however, that this is only an example. The invention may also be practiced with different values.

The invention claimed is:

1. A device for the inspection of an entire inspection range of a wafer or another flat object, said wafer or said object having a plane object surface comprising said entire inspection range, said device comprising:
   an object holder;
   a camera assembly with two or more cameras each for taking an image of at least a portion of said object in an imaging field;
   a driving assembly for the generation of a rotational movement between said camera assembly and said object from a first imaging position to at least one further imaging position;
   wherein said portions of said object each imaged by a different one of said cameras are at least partly different;
   wherein all of said cameras together simultaneously detect only a portion of said entire inspection range;
   wherein each object point of said entire inspection range is imaged at least once by one of said cameras due to said rotational movement between said camera assembly and said object;
   wherein said object, said object holder, or said camera assembly is rotatable about an axis perpendicular to said plane object surface; and
   wherein said image of said imaging fields of different of said cameras taken in different imaging positions are assembled to a common overall image.

2. The device of claim 1, and wherein said cameras of said camera assembly are statically mounted.

3. The device of claim 1, and wherein said cameras have an object plane and are provided with a plurality of detector elements each of said detector elements having a length and wherein said object, said object holder, said sensor chips with said detector elements, or said camera assembly are shiftable in a direction in said object plane by a distance, where a multiple of said distance corresponds to said length of said detector elements in said direction of said shifting distance.

4. The device according to claim 3, and wherein said object, said object holder, said sensor-chips with said detector elements, or said camera assembly are shiftable several times in two perpendicular directions in said object plane by distances where a multiple of such distances corresponds to said length of said detector elements in said directions of said corresponding shifting distances.

5. The device of claim 1, and wherein each of said cameras is provided with its own imaging optical assembly and its own detector.

6. The device of claim 1, and wherein said images are essentially telecentric.

7. The device of claim 5, and wherein an imaging path of light is defined by each of said imaging optical assemblies and one or more color- and/or infrared filters are provided in said imaging paths of light.

8. The device of claim 1 and wherein at least one light source is provided and an illumination path of light is defined by said light source and wherein one or more color- and/or infrared filters are provided in said illumination path of light.

9. A method for the inspection of an entire inspection range of a wafer or another flat object consisting of object points, said wafer or said object having a plane object surface comprising said entire inspection range, the method comprising the steps of:
simultaneously taking images of at least partly different portions of said object with different cameras of a camera assembly with at least two cameras, wherein all of said cameras together simultaneously detect only a portion of said entire inspection range of said object;
generating a rotational movement between said camera assembly and said object about an axis perpendicular to said plane surface from a first imaging position to at least one further suitable imaging position, where a further portion of said entire inspection range is detected; and
repeating the steps of taking images and generating a rotational movement until each object point of said entire inspection range is imaged at least once by one of said cameras; and
wherein said images of said portions of said object of different cameras in said camera assembly taken in different imaging positions are assembled to a common overall image.

10. The method of claim 9, and wherein said cameras have an object plane and are provided with a plurality of detector elements each of said detector elements having a length and wherein said object, said object holder, said sensor chips with said detector elements, or said camera assembly are shiftable in a direction in said object plane by a distance, where a multiple of said distance corresponds to said length of said detector elements in said direction of said shifting distance.

11. The method of claim 10, and wherein said distance of said distance is a quarter each of said length of said detector elements in said direction of said shifting.

12. The method of claim 10, and wherein said shift is carried out in two perpendicular directions.

13. The method of claim 9, and wherein said object, said object holder, or said camera assembly is rotated about an angle of 90°.

14. A device for the inspection of an entire inspection range of a wafer or another flat object, said wafer or said object having a plane object surface comprising said entire inspection range, said device comprising:
an object holder;
a camera assembly with two or more cameras each for taking an image of at least a portion of said object in an imaging field;
a driving assembly for the generation of a relative movement between said camera assembly and said object from a first imaging position to at least one further imaging position;
wherein said portions of said object each imaged by a different one of said cameras are at least partly different;
wherein all of said cameras together simultaneously detect only a portion of said entire inspection range;
wherein each object point of said entire inspection range is imaged at least once by one of said cameras due to said relative movement between said camera assembly and said object; and
wherein said cameras have an object plane and are provided with a plurality of detector elements each of said detector elements having a length and wherein said object, said object holder, said sensor chips with said detector elements, or said camera assembly are shiftable in a direction in said object plane by a distance, where a multiple of said distance corresponds to said length of said detector elements in said direction of said shifting distance.

15. The device of claim 1, and wherein the cameras of said camera assembly are positioned so that each image of said imaging fields of different of said cameras taken in different imaging positions are taken at the same measuring angle.

16. The device of claim 1, and wherein all respective cameras of said camera assembly are positioned directly above said portion of the plane object surface being imaged when being imaged by the respective camera.

17. The method of claim 9, and wherein the step of simultaneously taking images of at least partly different portions of said object with different cameras of a camera assembly with at least two cameras, includes the step of taking all of the images with the same measuring angle.

18. The method of claim 9, and wherein the step of simultaneously taking images of at least partly different portions of said object with different cameras of a camera assembly with at least two cameras, includes the step of taking all of the images from directly above the at least partly different portions of said object.

* * * * *